(12) United States Patent
Doyle et al.

(10) Patent No.: US 8,586,012 B2
(45) Date of Patent: *Nov. 19, 2013

(54) BODY WASH WITH SUNSCREEN SYSTEM AND METHOD

(75) Inventors: Michael Phillip Doyle, Carmel, CA (US); Royce Dale Lillard, II, Phoenix, AZ (US); Royce Dale Lillard, III, Phoenix, AZ (US); Richard J. Bertozzi, Marco Island, FL (US)

(73) Assignee: Solise LLC, Phoenix, AZ (US)

( * ) Notice: Subject to any disclaimer, the term of this patent is extended or adjusted under 35 U.S.C. 154(b) by 317 days.

This patent is subject to a terminal disclaimer.

(21) Appl. No.: 12/897,928

(22) Filed: Oct. 5, 2010

(65) Prior Publication Data

US 2011/0020253 A1 Jan. 27, 2011

Related U.S. Application Data

(63) Continuation-in-part of application No. 12/156,966, filed on Jun. 6, 2008, now Pat. No. 7,824,662.

(60) Provisional application No. 60/933,539, filed on Jun. 6, 2007.

(51) Int. Cl.
*A61K 8/92* (2006.01)
*A61Q 17/04* (2006.01)
*A61Q 19/10* (2006.01)
*A61K 8/84* (2006.01)

(52) U.S. Cl.
USPC ............ 424/60; 424/59; 424/64; 424/74; 424/70.31; 424/70.11; 510/159

(58) Field of Classification Search
USPC ............ 424/60, 59, 64, 74, 70.31, 70.11; 510/159
See application file for complete search history.

(56) References Cited

U.S. PATENT DOCUMENTS

| | | | | |
|---|---|---|---|---|
| 4,590,086 | A | * | 5/1986 | Takahashi et al. ............ 426/602 |
| 6,069,169 | A | * | 5/2000 | Ptchelintsev et al. ......... 514/532 |
| 7,824,662 | B2 | * | 11/2010 | Doyle et al. .................... 424/59 |
| 2006/0280702 | A1 | * | 12/2006 | SenGupta et al. .............. 424/59 |

* cited by examiner

*Primary Examiner* — Ernst Arnold
*Assistant Examiner* — Hong Yu
(74) *Attorney, Agent, or Firm* — Yee & Associates, P.C.

(57) ABSTRACT

A body wash composition includes sunscreen or UV screen materials. The body wash composition is formulated so that it may be applied during normal hygiene activities, such as washing. However, the composition applies an effective level of sunscreen or UV screen material to the body such that the sunscreen or UV screen continues to provide effective solar protection even after rinsing or washing of the human body. Further, the material is a non-greasy, easy to apply material that may be used during showering activities in a manner similar to using a bar soap or cleanser. The composition includes a variety of materials that assist in the processing and storage of the body wash. Effective amounts of solar protective material include octyl methoxycinnamate, octyl salicylate, and titanium dioxide. Testing shows that the product provides a solar protective level of at least approximately 14 even after multiple rinsings. Further embodiments have achieved a solar protective level of at least approximately 17.

19 Claims, 1 Drawing Sheet

BODY WASH WITH SUNSCREEN SYSTEM AND METHOD

CROSS REFERENCE TO RELATED APPLICATIONS

This application is a continuation in part of, and claims priority from, U.S. patent application filed on Jun. 6, 2008, Ser. No. 12/156,966, now issued as U.S. Pat. No. 7,824,662, which in turn claims priority from the U.S. provisional patent application Ser. No. 60/933,539 filed Jun. 6, 2007 in the names of Michael Doyle, Dale Lillard, Trace Lillard and Richard Bertozzi, and entitled "Body Wash With Sunscreen".

FIELD OF THE INVENTION

The present invention relates to body wash compositions. More particularly, the present invention relates to body wash compositions that include a sunscreen agent, and still more particularly, the invention relates to sunscreen additives which will not easily wash off the host's body.

BACKGROUND OF THE INVENTION

Humans can suffer various deleterious effects from overexposure to sunlight, including sunburn, aging of skin, wrinkling, and an increased risk of skin cancer. To avoid these effects, individuals who will be exposed to long periods of sunlight can cover their skin with sunscreen materials.

Personal care products like body washes are becoming more popular in the United States and around the world. Desirable body wash compositions should meet a number of criteria. For example, to be acceptable to consumers, a body wash should have many or all of the following characteristics: attractive appearance, acceptable scent, good lather, ability to leave the skin feeling soft and smooth, i.e., provide a skin conditioning benefit, be gentle to the skin, be easy to use and rinse off easily. Finally, it is desirable that the product provide some protection against the harmful rays of the sun.

Many consumers are aware of the harmful effects of the ultraviolet rays of the sun. An increase in skin cancer and photo-aging of the skin from excessive exposure to the sun's rays is widely known. As a result, many forms of sunscreen products are sold to provide varying degrees of protection. However, despite these many product choices, often consumers fail to apply such products on a regular basis. They are viewed many times as being inconvenient. Most people bathe or shower frequently, especially in the United States. To have a product used routinely in the bath or shower that would provide some level of sunscreen protection would be very convenient and highly desirable. Many products such as make-up, lip balm and even hair spray products now have SPF protection. Providing some level of protection from a body wash would be valuable.

Combining sunscreens and cleansers, both bars and liquids, has been attempted for quite some time. For example, Berstein (Jun. 12, 1990), in U.S. Pat. No. 4,933,174, describes a detergent (non-ionic and/or amphoteric) and sunscreen agents which claims to provide some amount of protection to the skin from ultraviolet light even after rinsing the product. However, it requires at least 12 applications to be effective.

Grieveson, et al. (Aug. 26, 1997), in U.S. Pat. No. 5,661,189, describes a liquid cleansing and moisturizing composition that contains benefit agents among which are sunscreens.

Gildenberg, et al. (Apr. 17, 2001), in U.S. Pat. No. 6,217,852, describes personal cleansing compositions having photo-protective agents that require at least one photo-protective agent to be encapsulated in a time-release capsule.

Kaufman and Dulak (Mar. 28, 2000), in U.S. Pat. No. 6,043,204, describes a body cleansing composition providing protection against sunburn after rinsing that requires at least one hydroxyethylated organic nitrogen compound fixative, a polymeric quaternary ammonium salt and at least one volatile organic liquid.

Morgan, et al. (May 1, 2001 and Jun. 4, 2002), in U.S. Pat. Nos. 6,224,852 and 6,399,045, describes liquid sunscreen compositions which both deposit and lather well that require cationic polymer.

Crookham, et al. (Jun. 10, 2003), in U.S. Pat. No. 6,576,228, describes personal wash sunscreen compositions which deposit and lather well that require water soluble sunscreens.

Traynor, et al. (Feb. 14, 2006), in U.S. Pat. Nos. 6,998,113 and 7,001,592, describes body washes containing additives including sunscreens that are encapsulated in sol-gel microcapsules.

Nevertheless, in spite of all the above attempts, there remains an unmet need for an effective body wash and sunscreen combination. There exists a need for a product that would provide an effective level of sun protection, particularly a level of sun block or sunscreen that is higher than existing formulations. Further, the body washes and sunscreen combination should remain effective even after rinsing. Moreover, the sun screening functionality should preferably remain effective even after multiple rinsings or washings. Additionally, it would be desired that a body wash and sunscreen product have a gentle or acceptable feel on the human skin, as opposed to an oily feel which characterizes prior art compositions. Still further, it would be desired that a combined body wash and sunscreen be packaged in a means that can be readily and easily delivered to a human consumer, such as in liquid or bar form. Hence, there has been identified a need to provide an improved product that combines body wash and sunscreen functionality. The present invention addresses one or more of these needs.

BRIEF DESCRIPTION OF THE DRAWINGS

The novel features believed characteristic of the invention are set forth in the appended claims. The invention itself, however, as well as a preferred mode of use, and further objectives and advantages thereof, will best be understood by reference to the following detailed description of an illustrative embodiment when read in conjunction with the accompanying drawings, wherein:

SUMMARY OF THE INVENTION

Attempts to make a body wash with sunscreen ingredients that would impart some level of ultraviolet radiation protection after normal use were numerous and unsuccessful. To determine if the concept was even possible, commercially purchased well-known body wash and sunscreen products were combined with vigorous mixing to produce a viscous liquid. After use, it was determined that some level of SPF protection was possible. Thereafter, combinations of selected sunscreen ingredients and surfactant mixtures were made with emulsifiers and skin care ingredients. It was discovered that certain sunscreens, which are effective against both UV-A and UV-B rays, when combined with selected anionic, nonionic and amphoteric surfactants and emulsifiers, produce a product which cleanses the body and provides SPF protection of 4 or greater after only 1-4 washes. Comments from several people who used the product indicated some protection after only a single use. Skin care ingredients were also added to leave the skin feeling soft and smooth. The product, despite containing up to 15% of primarily oil soluble sunscreens, lathered quite well and was stable. The product samples appear to be simple yet elegant. Achieving success in combining seemingly incompatible ingredients in a product that cleans yet deposits active materials was unexpected, especially after so many unsuccessful trials.

Unlike leave-on products, measuring the benefit of sunscreen ingredients applied from a body wash depends heavily upon the method of application. Since a body wash is generally used in the shower, the proper method of applying the product should be in the same manner as one would apply and use a bar of soap or liquid cleanser. Determining SPF of products prior to this invention used in-vitro methods (U.S. Pat. No. 6,576,228) or modified procedures from those outlined in the Federal Register volume 43 (1978) pages 38264-267 for measurement of SPF (FDA monograph C.F.R. 21). For example, in U.S. Pat. Nos. 6,224,852 and 6,399,045, a 50 square cm area of the back was used to apply and rinse the product and test for SPF. Likewise, in U.S. Pat. Nos. 6,998,113 and 7,001,592 a 50 square cm area of the test site was used for applying the product, rinsing it and exposing it to radiation per the FDA monograph. It should be noted that when the product of this invention was tested using this method on a small 5 person panel, the average SPF value obtained was 3 times higher than when the product was used normally.

It has now been surprisingly discovered that in creating a body wash with sunscreen, both the selective choice of ingredients and the manner in which the components are combined and blended, is important to achieve success in obtaining optimum performance. In one embodiment, a primary aqueous phase of surfactants, chelant and emollient/humectants adequately disperses titanium dioxide or other inorganic sunscreen pigment. Then an oil phase of sunscreens and oil soluble moisturizer and emollient and skin conditioner is added to the aqueous phase. A homogenization step is performed by addition of water/oil emulsifiers such that a uniform product is formed. Additionally, after fragrance, preservatives, and a viscosity modifier (or modifiers) are added, a third aqueous phase of oil/water emulsifiers is added with homogenization and mixing. This results in a stable, cosmetically elegant, off-white, viscous product being formed. This product was surprisingly found to provide SPF protection of greater than approximately 15 to 17 SPF after only a 10 second wash followed by a 5 second water rinse.

There is now provided a body wash composition that includes sunscreen or UV screen materials. The body wash composition is formulated so that it may be applied during normal hygiene activities, such as washing. However, the composition applies an effective level of sunscreen or UV screen material to the body such that the sunscreen or UV screen continues to provide effective solar protection even after rinsing or washing of the human body. Further, the material is a non-greasy, easy to apply material that may be used during showering activities in a manner similar to a bar soap or cleanser. The product may be applied by hand, washcloth, or any cleansing article such as brush, loofah, pouf, sponge, etc. However, it is particularly effective when applied with a loofah, pouf, or similar applicator device whereby the product produces copious amounts of lather. The composition includes a variety of materials that assist in the processing and storage of the body wash. Effective amounts of solar protective material include, but are not limited to, octyl methoxycinnamate, octyl salicylate, and titanium dioxide. Testing shows that the product provides a solar protective level of at least approximately 14 even after multiple rinsings.

In a further illustrative embodiment of the present invention, a method for creating a body wash with sunscreen is illustrated in a series of steps. One step includes blending water, with a first component of tetrasodium ethylenediaminetetracetate tetrahydrate, a second component of at least one of propylene glycol, diazolidinyl urea, and methylparaben and/or propylparaben, a third component of PEG 400, a fourth component of carbomer, and a fifth component of at least one of sodiuim laureth sulfate, cocamide DEA, and cocamidopropyl betaine, so as to create a first water phase. A further step includes blending at approximately 130 degrees F. dodecanoic acid, soy oil, 3,3,5-trimethylcyclohexyl 2-hydroxybenzoate, octyl methoxycinnamate, benzophenone-3, octylsalicylate, PEG-30 dipolyhydroxystearate, and titaniuim dioxide, so as to create a first oil phase. A still further step includes combining the first water phase with the first oil phase so as to create an emulsion. Still, a further step includes blending water with glyceryl stearate and PEG 100 stearate so as to create a second water phase; and a still further step includes blending the emulsion with the second water phase so as to create a body wash with sunscreen product.

The step of blending water with a first component, a second component, a third component, a fourth component, and a fifth component so as to create a first water phase may be performed at approximately 160 degrees F. as an initial temperature and ends at approximately 135 degrees F. The step of blending so as to create a first oil phase may be performed at approximately 130 degrees F. The step of blending so as to create a first oil phase further comprises combining the dodecanoic acid, the soy oil, the 3,3,5-trimethylcyclohelxyl 2-hydroxybenzoate, the octyl methoxycinnamate, the benzophenone-3, and the octyl salicylate components while heating to approximately 130 degrees F. so as to homogenize the blend and form a uniform blend, adding PEG-30 dipolyhydroxystearate to the blend and mixing, and then dispersing titanium dioxide into the blend with high shear mixing. Further, the step of combining the first water phase with the first oil phase may be performed such that the first water phase is at approximately 135 degrees F. and the first oil phase is at approximately 130 degrees F. when combined. The combination my now be milled from approximately 10 to approximately 15 minutes.

In still a further illustrative embodiment of the present invention, a method of applying a body wash with sunscreen includes steps of applying to a user's body a body wash with sunscreen composition and rinsing the composition.

Other independent features and advantages of the body wash with sunscreen will become apparent from the following detailed description, taken in conjunction with the accompanying drawings which illustrate, by way of example, the principles of the invention.

DETAILED DESCRIPTION OF A PREFERRED EMBODIMENT

The following detailed description of the invention is merely exemplary in nature, and is not intended to limit the invention or the application and uses of the invention. Furthermore, there is no intention to be bound by any theory presented in the preceding background of the invention or the following detailed description of the invention. Reference will now be made in detail to exemplary embodiments of the invention.

The following are examples of a composition with a body wash also containing sunscreen ingredients. A variety of surfactants may be used for the cleansing component and would be known to those skilled in the art. Likewise, other emulsifiers, carefully selected, could be used to create a stable product. A wide variety of skin care ingredients could also be used and would be known to those skilled in the art. Finally, sunscreen agents should preferably be organic compounds of limited water solubility and include both UV-A and UV-B protection materials.

A further embodiment of a blending process is described as follows:

Phase I

Heat water to approximately 160 degrees F., and add components 2, 3 and 4 to the water. Mix for approximately 2 minutes. Add component 5 and homogenize until there are no lumps. This will take about 20 minutes. Then add component 6 and mix for approximately 10 minutes. The ending temperature should be about 135 degrees F. The first water phase may be set aside while further steps proceed.

| Order | Component | Chemical Name | % By Wt. |
|---|---|---|---|
| 1 | De-ionized water | De-ionized water | 43.30 |
| 2 | Versene 220 | Tetrasodium ethhylenediaminetetraacetate tetrahydrate | 0.20 |
| 3 | Germaben II | Propylene Glycol (and) Diazolidinyl Urea (and) Methylparaben (and) Propylparaben | 1.00 |
| 4 | PEG 400 | PEG 400 | 2.00 |
| 5 | Carbopol 940 | Carbomer | 0.40 |
| 6 | Sulfochem B-DEV | Sodium Laureth Sulfate (and) Cocamide DEA (and) Cocamidopropyl Betaine | 30.00 |

Phase II

Combine components 7, 8, 9, 10, 11 and 12 while heating to about 130 degrees F. Mix in order to homogenize the materials. Then add component 13, mix for approximately 5 minutes. Then add component 14, mix for approximately 5 minutes. Micronized titanium dioxide may be used. The first oil phase may be set aside while other steps proceed.

| Order | Component | Chemical Name | % By Wt. |
|---|---|---|---|
| 7 | Lauric Acid | Dodecanoic Acid | 1.50 |
| 8 | Soy Oil | Soy oil | 1.50 |
| 9 | Homosalate | 3,3,5-Trimethylcyclohexyl 2-hydroxybenzoate | 4.00 |
| 10 | Octyl Methoxycinnamate | Octyl methoxycinnamate | 3.75 |
| 11 | Oxybenzone | Benzophenone-3 | 3.00 |
| 12 | Octyl salicylate | Octyl salicylate | 2.50 |
| 13 | Arlacel P-135 | PEG-30 dipolyhydroxystearate | 0.10 |
| 14 | Titanium dioxide | Titanium dioxide | 0.10 |

At this point, the oil phase material is combined with the water phase material. Blending of these materials results in an emulsion. Phase I is preferably at about 135 degrees F., and phase 2 is preferably at about 130 degrees F. when the oil phase and the water phase are combined. The resulting emulsion may be milled for approximately 10-15 minutes.

Phase III

Heat water, component 15, to approximately 185 degrees F. Add component 16 to the water and mix until dissolved. Add the resulting phase III, a second water phase, to the emulsion above and mix until dissolved. Continue mixing until the temperature drops to approximately 110 degrees F. and add component 17. The fragrance may be an herbal fragrance. Continue mixing until the temperature reaches approximately 105 degrees F.

| Order | Component | Chemical Name | % By Wt. |
|---|---|---|---|
| 15 | De-ionized water | De-ionized water | 6.00 |
| 16 | RitaPro 165 | Glyceryl stearate (and) PEG 100 | 0.30 |
| 17 | Fragrance | Fragrance | 0.35 |

The completed product should be off white and smooth.

Range of material. The following chart lists the materials from the above composition and also provides an approximate range by weight percentage for the materials in the finished body wash with sunscreen composition.

| Order | Component | Chemical Name | % By Wt. |
|---|---|---|---|
| 1 | De-ionized water | De-ionized water | balance |
| 2 | Versene 220 | Tetrasodium ethhylenediaminetetraacetate tetrahydrate | 0.10-0.50 |
| 3 | Germaben II | Propylene Glycol (and) Diazolidinyl Urea (and) Methylparaben (and) Propylparaben | 0.25-1.50 |
| 4 | PEG 400 | PEG 400 | 1.00-10.00 |
| 5 | Carbopol 940 | Carbomer | 0.20-1.00 |
| 6 | Sulfochem B-DEV | Sodium Laureth Sulfate (and) Cocamide DEA (and) Cocamidopropyl Betaine | 10.00-60.00 |
| 7 | Lauric Acid | Dodecanoic Acid | 0.50-5.00 |
| 8 | Soy Oil | Soy oil | 0.50-5.00 |
| 9 | Homosalate | 3,3,5-Trimethylcyclohexyl 2-hydroxybenzoate | 2.00-6.00 |
| 10 | Octyl Methoxycinnamate | Octyl methoxycinnamate | 2.00-6.00 |
| 11 | Oxybenzone | Benzophenone-3 | 2.00-6.00 |
| 12 | Octyl salicylate | Octyl salicylate | 2.00-6.00 |
| 13 | Arlacel P-135 | PEG-30 dipolyhydroystearate | 0.10-2.00 |
| 14 | Titanium dioxide | Titanium dioxide | 0.00-4.00 |
| 15 | De-ionized water | De-ionized water | |
| 16 | RitaPro 165 | Glyceryl stearate (and) PEG 100 | 0.10-3.00 |
| 17 | Fragrance | Fragrance | 0.0-2.50 |

The Arlacel in the above formulations can be substituted. In a first optional formulation, the amount of Arlacel is substituted with a blend of approximately 60 wt % sorbitan monosterate and approximately 40 wt % sorbitan monopalmitate. The monosterate is available under the trade name Span 60 from Uniqema Americas, and the monopalmitate is sold under the trade name Span 40 also from Uniqema Americas.

In a second optional formulation, the Arlacel is substituted by a blend of approximately 55 wt % sorbitan monolaurate and approximately 45 wt % sorbitan trioleate. These materials are sold under the trade names span 20 and Span 85 respectively, again offered by Uniqema Americas. Other combinations of emulsifiers may be used to provide similar HLB values.

A second preferred embodiment is prepared in the following steps and formulation.

Phase I

Heat water to approximately 160 degrees F., then add components 2, 3 and 4. Mix for approximately 2 minutes. Add component 5 and continue mixing so as to homogenize. Preferably, there are no lumps in the resulting blend. This may take about 20 minutes of mixing. Then add component 6 and mix for approximately 10 minutes. The ending temperature should be about 135 degrees F.

| Order | Component | Chemical Name | % By Wt. |
|---|---|---|---|
| 1 | De-ionized water | De-ionized water | 41.10 |
| 2 | Versene 220 | Tetrasodium ethhylenediaminetetraacetate tetrahydrate | 0.20 |
| 3 | Germaben II | Propylene Glycol (and) Diazolidinyl Urea (and) Methylparaben (and) Propylparaben | 1.00 |
| 4 | PEG 400 | PEG 400 | 2.00 |
| 5 | Carbopol 940 | Carbomer | 0.40 |
| 6 | Sulfochem B-DEV | Sodium Laureth Sulfate (and) Cocamide DEA (and) Cocamidopropyl Betaine | 31.00 |

Phase II

Combine components 7, 8, 9, 10, 11 and 12 while heating to about 130 degrees F. to homogenize. Then add components 13 and 14, mix for approximately 5 minutes. Then add component 15, mix for approximately 5 minutes.

| Order | Component | Chemical Name | % By Wt. |
|---|---|---|---|
| 7 | Lauric Acid | Dodecanoic Acid | 1.50 |
| 8 | Soy Oil | Soy oil | 1.50 |
| 9 | Homosalate | 3,3,5-Trimethylcyclohexyl 2-hydroxybenzoate | 4.00 |
| 10 | Octyl Methoxycinnamate | Octyl methoxycinnamate | 3.75 |
| 11 | Oxybenzone | Benzophenone-3 | 3.00 |
| 12 | Octyl salicylate | Octyl salicylate | 2.50 |
| 13 | Span 20 | Sorbitan monolaurate | 0.055 |
| 14 | Span 85 | Sorbitan trioleate | 0.045 |
| 15 | Titanium dioxide | Titanium dioxide | 2.00 |

At this point, the oil phase material is combined with the water phase material. The oil phase and water phase are mixed together so as to create an emulsion. Phase 1 is preferably at about 135 degrees F., and phase 2 is preferably at about 130 degrees F. when combined. The emulsion may be milled for approximately 10-15 minutes.

Phase III

Heat water, component 16, to approximately 165 degrees F. Add component 17 and mix until dissolved. Add the resulting water phase to the emulsion above and mix until dissolved. Mix till temp drops to 110 F and add component 18. Mix till temp is 105 F. The completed product should be off white in color and should be smooth in texture.

| Order | Component | Chemical Name | % By Wt. |
|---|---|---|---|
| 16 | De-ionized water | De-ionized water | 6.00 |
| 17 | RitaPro 165 | Glyceryl stearate (and) PEG 100 | 0.30 |
| 18 | Fragrance | Fragrance | 0.34 |

Range of material. The following chart lists the materials from the above composition and also provides a range by weight percentage for the materials.

| Order | Component | Chemical Name | % By Wt. |
|---|---|---|---|
| 1 | De-ionized water | De-ionized water | balance |
| 2 | Versene 220 | Tetrasodium ethhylenediaminetetraacetate tetrahydrate | 0.10-0.50 |
| 3 | Germaben II | Propylene Glycol (and) Diazolidinyl Urea (and) Methylparaben (and) Propylparaben | 0.25-1.50 |
| 4 | PEG 400 | PEG 400 | 1.00-10.00 |
| 5 | Carbopol 940 | Carbomer | 0.20-1.00 |
| 6 | Sulfochem B-DEV | Sodium Laureth Sulfate (and) Cocamide DEA (and) Cocamidopropyl Betaine | 10.00-60.00 |
| 7 | Lauric Acid | Dodecanoic Acid | 0.50-5.00 |
| 8 | Soy Oil | Soy oil | 0.50-5.00 |
| 9 | Homosalate | 3,3,5-Trimethylcyclohexyl 2-hydroxybenzoate | 2.00-6.00 |
| 10 | Octyl Methoxycinnamate | Octyl methoxycinnamate | 2.00-6.00 |
| 11 | Oxybenzone | Benzophenone-3 | 2.00-6.00 |
| 12 | Octyl salicylate | Octyl salicylate | 2.00-6.00 |
| 13 | Span 20 | Sorbitan monolaurate | 0.01-1.00 |
| 14 | Span 85 | Sorbitan trioleate | 0.01-1.00 |
| 15 | Titanium dioxide | Titanium dioxide | 0.00-4.00 |
| 16 | De-ionized water | De-ionized water | |
| 17 | RitaPro 165 | Glyceryl stearate (and) PEG 100 | 0.10-3.00 |
| 18 | Fragrance | Fragrance | 0.0-2.50 |

Figure 1:
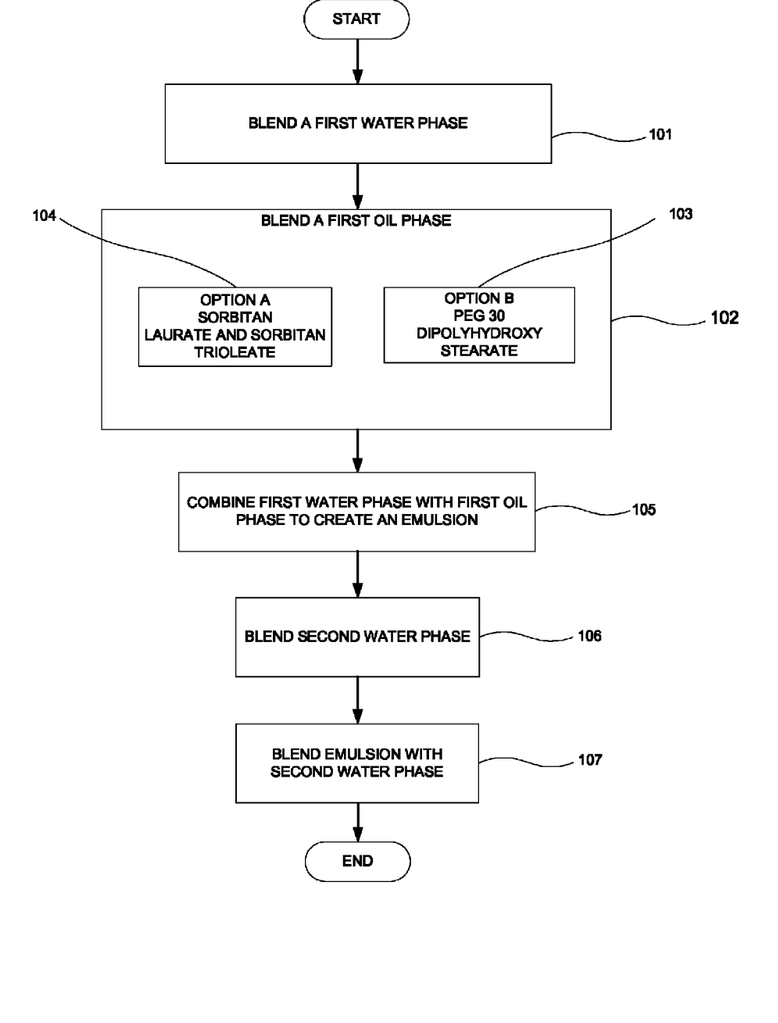
FIG. 1 is a flowchart of a blending process wherein a body wash with sunscreen composition may be created in accordance with an illustrative embodiment.

Referring now to FIG. 1, a flowchart depicting steps in a method to create a body wash with sunscreen composition is described. In one step, a first water phase is blended (step 101). In this step, water is heated, preferably to approximately 160 degrees F. Heating may preferably include heating water to at least approximately 130 degrees F. Components such as Versene 220, Germaben II, and PEG 400 are then introduced into the water and mixed for a short period, such as approximately 2 minutes. Carbopol 940 is then introduced into the mixture, and the mixture is further blended so as to homogenize the mixture. This mixing may take approximately 20 minutes. The Sulfochem B-DEV is then introduced into the mixture, and the mixture is further mixed. The further mixing may proceed for approximately 10 minutes. Preferably, after all mixing the ending temperature of the water phase is approximately 135 degrees F.

In a further step, a first oil phase is blended (step 102). The oil phase has alternative compositions and correspondingly alternative blending steps. In one composition, option B, Arlacel is used, which corresponds to PEG 30 dipolyhydroxy stearate (step 103). In an alternative formulation, option A, Span 20 and Span 85 are used, which correspond to sorbitan monolaurate and sorbitan trioleate (step 104).

The first oil phase comprises combining and mixing the emollients, soy oil and dodecanoic acid and the sunscreens, 3,3,5-trimethylcyclohexyl 2-hydroxybenzoate, ocryl methoxycinnamate, benzophenone-3 and octyl salicylate while heating to approximately 130 degrees F. Preferably, the first oil phase is prepared with components heated to approximately at least 120 degrees F. The mixing continues so as to produce a uniform blend. PEG 30 dipolyhydroxystearate is further added to the blend with further mixing according to Option B. Option A would include Span 20 and Span 85 materials in place of Arlacel. Titanium dioxide is then dispersed into the blend with continued mixing, which may continue for approximately 5 minutes.

It is noted that steps 101 and 102 may proceed in alternative processing modes. For example, the first water phase and the first oil phase may be created simultaneously, or approximately simultaneously. Alternatively, a first water phase may be created in series with the first oil phase. Alternatively, the first oil phase may be created, followed by creation of the first water phase in series.

In a further processing step, the first water phase is combined with the first oil phase so as to create an emulsion (step 105). At this point, the oil phase material is combined with the water phase material. Blending the combined phases results in an emulsion. When combining the first oil phase and the first water phase, it should be done at an elevated temperature of from approximately 100 degrees F. to approximately 170 degrees F., more preferably of from approximately 120 degrees F. to approximately 150 degrees F., and even more preferably from approximately 130 degrees F. to approximately 135 degrees F. In a further preferred embodiment, when combined, the first water phase should be about 135 degrees F., and the first oil phase should be about 130 degrees F.

The emulsion may be milled for a period of from approximately 5 to approximately 60 minutes, more preferably, for a period of from approximately 5 minutes to approximately 30 minutes, and even more preferably from approximately 10 to approximately 15 minutes.

In a further step, a second water phase is blended (step 106). This step proceeds with heating a further portion of water to approximately 185 degrees F. A component of RitaPro 165, which corresponds to glyceryl stearate and PEG 100, is mixed with the heated water until dissolved. Optionally, a fragrance may be added to the second water phase.

It is also noted that steps 105 and 106 may proceed in alternative processing modes such as proceeding in parallel or in series.

In a further step, the second water phase is blended into the emulsion (step 107). The blending of this step preferably proceeds with high shear mixing until a uniform body wash with sunscreen product is created. Preferably, a finishing temperature is approximately 105 degrees F. Optionally, a fragrance, such as an herbal fragrance, may be blended into the product at this time.

In a further embodiment of formulating a body wash with sunscreen, a body wash product with high efficacy SPF protection comprises a primary aqueous phase of surfactants, emollients(s) and chelant, a secondary oil phase of sunscreens, oil soluble emollients, and skin conditioners; water in oil emulsifiers, and a tertiary aqueous phase of oil in water emulsifiers. Specifically, to the mixed primary aqueous phase, inorganic sunscreen is added slowly and mixed thoroughly. With homogenization, the secondary oil phase is added to the aqueous phase followed by the addition of water in oil emulsifiers while continuing homogenization. After further addition of preservative, fragrance, and viscosity modifier(s) with only mixing, the tertiary aqueous phase of oil in water emulsifier is added and homogenization is again begun. Homogenization may continue for approximately 20 minutes to complete the process. The resulting product is a creamy off white, viscous, oil in water emulsion.

A third preferred embodiment is prepared in the following steps and formulation. In this preferred embodiment, the process is carried out at an approximately constant temperature that can vary between approximately 100 degrees F. to approximately 185 degrees F.

Phase I

To heated water, add components 2 and 3 and mix until dissolved. Add component 4 and continue mixing until a uniform blend is achieved. Slowly add component 5 and mix until dispersed uniformly

| Order | Component | Chemical Name | % By Wt. |
|---|---|---|---|
| 1 | De-ionized water | De-ionized water | 38.15 |
| 2 | Versene 220 | Tetrasodium ethhylenediaminetetraacetate tetrahydrate | 0.20 |
| 3 | PEG 400 | Polyethylene glycol 400 | 2.00 |
| 4 | Sulfochem B-MEV | Sodium Laureth Sulfate (and) Cocamide MEA (and) Cocamidopropyl Betaine | 35.00 |
| 5 | T-Lite SF-S | Titanium dioxide (and) hydrated silica (and) aluminum hydroxide (and) dimethicone/methicone copolymer | 2.00 |

Phase II

Separately, combine components 6, 7, 8, 9, 10, and 11 and mix until a homogeneous blend is formed.

| Order | Component | Chemical Name | % By Wt. |
|---|---|---|---|
| 6 | Lauric Acid | Dodecanoic Acid | 1.50 |
| 7 | Soy Oil | Soy oil | 1.00 |
| 8 | Homosalate | 3,3,5-Trimethylcyclohexyl 2-hydroxybenzoate | 4.00 |
| 9 | Octinoxate | Octyl methoxycinnamate | 3.75 |
| 10 | Oxybenzone | Benzophenone-3 | 3.00 |
| 11 | Octisalate | Octyl salicylate | 2.50 |

Add Phase II to Phase I with mixing. To the combined Phase I and Phase II mixture, add components 12 and 13 and homogenize to create an emulsion. After the emulsion is formed, while mixing, add component 14, then add component 15. Slowly add component 16 and homogenize until a uniform consistency is achieved.

| Order | Component | Chemical Name | % By Wt. |
|---|---|---|---|
| 12 | Span 20 | Sorbitan monolaurate | 0.055 |
| 13 | Span 85 | Sorbitan trioleate | 0.045 |
| 14 | Euxyl K 100 | Benzyl alcohol (and) methylchloroisothiazolinone (and) methylisothiazolinone | 0.10 |
| 15 | Fragrance | Fragrance | 0.30 |
| 16 | Xanthan Gum | Xanthan Gum | 0.10 |

Phase III

To heated water, component 17, add and dissolve component 18.

| Order | Component | Chemical Name | % By Wt. |
|---|---|---|---|
| 17 | De-ionized water | De-ionized water | 6.00 |
| 18 | RitaPro 165 | Glyceryl stearate (and) PEG 100 | 0.30 |

Combine Phase III with the emulsion blend and homogenize to form the final emulsion. Discontinue homogenization and continue mixing for approximately 10 minutes to create a creamy off-white product that is smooth in texture.

The above formulations and the methods of creating the formulations may be generalized in the following preferred embodiment. A method for creating a body wash with sunscreen includes a process which is carried out at an approximately constant temperature ranging from about 100 degrees F. to about 185 degrees F. The method includes the steps of blending water with a chelant, humectants/skin conditioner, at least one anionic and/or nonionic and/or amphoteric surfactant followed by dispersing titanium dioxide (or other inorganic sunscreen) so as to create a first water phase. A further step includes blending an emollient/skin conditioning fatty acid, an emollient/skin conditioning oil, a first organic sunscreen such as homosalate, a second organic sunscreen such as Octinoxate, a third organic sunscreen such as Oxybenzone and a fourth organic sunscreen such as Octisalate so as to form an oil phase. In a still further step, combine the oil phase with the first water phase and add water in oil emulsifiers so as to create an emulsion. In a further step, preservatives, fragrance, and a viscosity modifier may be added to the emulsion. A further step includes blending water with oil in water emulsifiers to create a second water phase. In a further step the second water phase is blended into the emulsion so as to create a body wash with sunscreen product. The components in the body wash with sunscreen product are present in the final product in the following approximate amounts by weight percent:

| Order | Component | % By Wt. |
|---|---|---|
| 1 | De-ionized water | balance |
| 2 | Chelant | 0.10-0.50 |
| 3 | Humectant/Skin Conditioner | 1.00-10.00 |
| 4 | Surfactants | 10.00-50.00 |
| 5 | Titanium dioxide | 0.0-4.00 |
| 6 | Emollient/Skin Conditioning Fatty Acid | 0.50-5.00 |
| 7 | Emollient/Skin conditioning oil | 0.50-5.00 |
| 8 | Organic Sunscreen A | 2.00-6.00 |
| 9 | Organic Sunscreen B | 2.00-6.00 |
| 10 | Organic Sunscreen C | 2.00-6.00 |
| 11 | Organic Sunscreen D | 2.00-6.00 |
| 12 | Emulsifiers (water in oil) | 0.02-3.00 |
| 13 | | |
| 14 | Preservatives | 0.05-1.75 |
| 15 | Fragrance | 0.0-2.50 |
| 16 | Viscosity modifiers(s) | 0.01-1.00 |
| 17 | | |
| 18 | Emulsifier(s) (oil in water) | 0.10-3.00 |

In the generalized embodiment, a class or family of chemicals is noted that may be used whereas specific preferred chemicals are noted in other preferred embodiments. Those skilled in the art will recognize that a family of related chemicals may provide similar functionality such that a certain level of substitutability or equivalence may be expected. For example, chelants or chelating agents may be selected from a variety of available products for use in personal care products. Chelating agents may include EDTA, DTPA, HEDTA, GLDA or EDG. The preferred component is tetrasodium ethylenediamintetraacetate tetrahydrate.

The humectants/skin conditioner may be selected from a wide variety of materials including glycerin, saccharides and polysaccharides, ethoxylated alcohols or glycols. The preferred component is polyethylene glycol 400.

The surfactant may be selected from a wide variety of materials designed for use in personal care products. A preferred component is the combination of sodium laureth sulfate and cocamide MEA and cocamidopropyl betaine.

Titanium dioxide may be of various types, both micronized and non-micronized, and with adjunctive minor ingredients. Of particular benefit and a preferred component is titanium dioxide and hydrated silica and dimethicone/methicone copolymer and aluminum hydroxide. Other kinds of inorganic sunscreen may also be used such as for example zinc oxide.

Emollients may be selected from a wide variety of materials including fats and oils, silicone oils, essential fatty acids, fatty alcohols and their esters, lanolin and lanolin esters. Preferred components are lauric acid and soy oil.

Sunscreen materials may be of various types. UV screens of both UV-A and UV-B types may be complex organic materials and may vary considerably. Preferred organic sunscreen components are homosalate, Octinoxate, Oxybenzone, and Octisalate. In general it has been found that combinations of varied inorganic and organic sunscreens provide a wide level or protection against both UV-A and UV-B. However, in other embodiments, rather than using Organic Sunscreens A, B, C, and D, it is also possible to use combinations of one or more organic sunscreens.

Preservatives may be selected from a variety of materials suited for use in personal care products. These include parabens, urea derivatives, isothiazolones, halogen—organic additives and organic acids and others. Preferred components are benzyl alcohol and methylchloroisothiazolinone and methylisothiazolinone.

Viscosity modifiers may be selected from a variety of materials including celluslosic derivatives, polyacrylic derivatives, clays and gums. A preferred component is Xanthan gum.

Emulsifiers, both water in oil and oil in water, may also be selected from a wide variety of materials to produce specific HLB values. Preferred emulsifiers are sorbitan monolaurate, sorbitan monopalmitate, sorbitan monostearate, and sorbitan trioleate as W/O emulsifiers. Glyceryl stearate and polyethylene glycol 100 stearate are preferred as O/W emulsifiers.

The third embodiment also comprises a composition or formulation having the following composition component ranges, by approximate weight per cent from lower value to upper value.

| Order | Component | Chemical Name | % By Wt. |
|---|---|---|---|
| 1 | De-ionized water | Water | balance |
| 2 | Versene 220 | Tetrasodium ethhylenediaminetetraacetate tetrahydrate | 0.10-0.50 |
| 3 | PEG 400 | Polyethylene glycol 400 | 1.00-10.00 |
| 4 | Sulfochem B-MEV | Sodium Laureth Sulfate (and) Cocamide MEA (and) Cocamidopropyl Betaine | 10.00-50.00 |
| 5 | T-Lite SF-S | Titanium dioxide (and) hydrated silica (and) aluminum hydroxide (and) dimethicone/methicone copolymer | 0.0-4.00 |
| 6 | Lauric Acid | Dodecanoic Acid | 0.50-5.00 |
| 7 | Soy Oil | Soy oil | 0.50-5.00 |
| 8 | Homosalate | 3,3,5-Trimethylcyclohexyl 2-hydroxybenzoate | 2.00-6.00 |
| 9 | Octinoxate | Octyl methoxycinnamate | 2.00-6.00 |
| 10 | Oxybenzone | Benzophenone-3 | 2.00-6.00 |
| 11 | Octisalate | Octyl salicylate | 2.00-6.00 |
| 12 | Span 20 | Sorbitan monolaurate | 0.01-1.50 |
| 13 | Span 85 | Sorbitan trioleate | 0.01-1.50 |
| 14 | Euxyl K 100 | Benzyl alcohol (and) methylchloroisothiazolinone (and) methylisothiazolinone | 0.05-1.75 |
| 15 | Fragrance | Fragrance | 0.0-2.50 |
| 16 | Xanthan Gum | Xanthan Gum | 0.01-1.00 |
| 17 | De-ionized water | De-ionized water | |
| 18 | RitaPro 165 | Glyceryl stearate (and) PEG 100 | 0.10-1.50 |

Testing Method of Present Invention

The product of this invention was tested by an independent testing laboratory following Good Laboratory Practices and was based on the method outlined in the Food and Drug Administration (FDA) Final Monograph for sunscreen testing published in the Federal Register, Vol. 64, No. 98, May 21, 1999. Concurrently with the test material, a standard sunscreen preparation of 8% Homosalate with a mean SPF value of 4.74+/−0.54, as shown in Table 1, was tested.

Test subjects (20) were assigned either the test product or an unidentified well-known commercially available body wash according to a generated randomization schedule. They were instructed to discontinue the use of their regular cleansing and/or body wash products. All subjects were advised not to introduce any new personal care products, moisturizers or cosmetics during the study interval. They used the products during morning showering for three mornings in succession, washing and rinsing as with any liquid body wash. This was accomplished by working the product into a lather applying by hand, sponge or washcloth. After showering again with the product on the fourth morning, they were tested after 1 hour. Prior to receiving the alternate test product, all subjects used their regular cleansing products for 5 consecutive days as a rest interval. Results indicated an average SPF value for the test product of 4.74+/−0.54.

The sunscreen/body wash was also tested for SPF capability as follows: 50 cm.sup.2 of testing site was wetted with 10 ml of water delivered with a syringe. The test sample was applied as per FDA monograph C.F.R. 21 to the area. Lather was worked into the subject for 3 minutes to allow the product to absorb into the skin. The area was rinsed after 2 additional minutes with 20 ml of water, then the area was patted dry and allowed 15 minutes before exposure to radiation as per FDA monograph. The skin was exposed to UV radiation and the MED was noted and compared to the MED for skin without treatment. Results are shown in Table 2.

TABLE 1

Individual SPF Values

| Subject #6234 Number | Subject Initials | Subject ID # | Skin Type | Age | Sex | 8% HMS Standard | Sample Body Wash |
|---|---|---|---|---|---|---|---|
| 1 | * | * | * | * | * | * | * |
| 2 | EA | 8026 | III | 56 | F | 4.4 | 5.0 |
| 3 | JS | 15288 | III | 26 | F | 4.4 | 4.5 |
| 4 | DD | 15575 | II | 51 | M | 4.4 | 5.0 |
| 5 | JM | 52377 | II | 39 | M | 5.0 | 4.0 |
| 6 | LS | 6974 | III | 59 | F | 4.4 | 5.0 |
| 7 | TL | 23195 | III | 39 | M | 5.0 | 5.0 |
| 8 | MM | 33356 | II | 41 | F | 4.0 | 4.0 |
| 9 | BR | 13187 | II | 54 | F | 5.0 | 4.5 |
| 10 | VT | 16578 | III | 40 | F | 5.0 | 4.5 |
| 11 | DT | 11721 | II | 46 | F | 5.0 | 6.3 |
| 12 | KT | 207 | II | 34 | F | 4.4 | 5.0 |
| 13 | DM | 53579 | II | 50 | F | 5.0 | 4.5 |
| 14 | GM | 31667 | II | 39 | F | 5.0 | 4.5 |
| 15 | CS | 27351 | II | 57 | F | 4.4 | 4.5 |
| 16 | KP | 50612 | III | 45 | F | 5.0 | 4.5 |
| 17 | AH | 39455 | III | 39 | F | 4.4 | 4.5 |
| 18 | RL | 53968 | III | 52 | M | 5.0 | 5.0 |
| 19 | MR | 494 | II | 51 | F | 5.0 | 4.0 |
| 20 | TP | 12791 | II | 52 | M | 5.0 | 5.0 |
| 21 | CM | 42362 | II | 48 | F | 5.0 | 5.5 |
| Average SPF (n = 20) | | | | | | 4.74 | 4.74 |
| Standard Deviation | | | | | | 0.34 | 0.54 |
| Standard Error | | | | | | 0.08 | 0.12 |
| t (one-tail) | | | | | | 1.729 | 1.729 |
| A | | | | | | 0.13 | 0.21 |
| SPF Label | | | | | | 4.61 | 4.53 |

TABLE 2

Individual SPF Values

| Subject #6234 Number | Subject Initials | Subject ID # | Skin Type | Age | Sex | 8% HMS Standard | Sample Body Wash |
|---|---|---|---|---|---|---|---|
| 1 | SA | 9644 | II | 43 | F | 4.4 | 18.0 |
| 2 | CM | 18105 | II | 51 | F | 4.0 | 13.7 |
| 3 | VS | 8800 | III | 55 | F | 4.4 | 15.0 |

TABLE 2-continued

Individual SPF Values

| Subject #6234 Number | Subject Initials | Subject ID # | Skin Type | Age | Sex | 8% HMS Standard | Sample Body Wash |
|---|---|---|---|---|---|---|---|
| 4 | ML | 7123 | II | 44 | F | 4.0 | 13.7 |
| 5 | PN | 52982 | II | 51 | F | 4.4 | 15.0 |
| Average SPF (n = 5) | | | | | | 4.24 | 15.08 |
| Standard Deviation | | | | | | 0.22 | 1.76 |
| Standard Error | | | | | | 0.10 | 0.79 |
| t (one-tail) | | | | | | 2.132 | 2.132 |
| A | | | | | | 0.21 | 1.68 |
| SPF Value | | | | | | 4 | 13 |

This Example demonstrates that the sunscreen/body wash enhanced the sun protection as measured by this protocol, as compared to untreated skin, by an average SPF of over 15.

Testing was also performed on the second preferred formulation. The second formulation achieved an SPF score of between approximately 12 and 16. It is further to be appreciated that the second formulation was tested under procedures wherein the body wash composition was applied during a cleansing procedure such as showering, and the applied material was also subjected to multiple rinsings. However, the measured SPF score was still recorded at between 12 and 16 even after such washings and rinsings. It is not believed that other products now commercially available are measured in this manner. Thus, the preferred formulation achieves an effective level of measured sun blockage even after rinsings.

Testing was also performed on the third preferred embodiment formulation. The test sites were wetted with 10 ml of water delivered with a syringe. A 2 mg/square cm portion of the test sample was weighed and applied to the appropriate test site of the subject. Lather was worked into the subject for 10 seconds. The area was then rinsed for 5 seconds with 20 ml of water and the area patted dry. The average SPF value was over 17 as shown in the results summarized in Table 3.

TABLE 3

Individual SPF Values

| Subject Number | Subject Initials | Subject ID # | Skin Type | Age | Sex | 8% HMS Standard | Hand and Body Wash with Sunscreen |
|---|---|---|---|---|---|---|---|
| 1 | EG | 30870 | III | 48 | F | 4.4 | 17.1 |
| 2 | * | * | * | * | * | * | * |
| 3 | * | * | * | * | * | * | * |
| 4 | LK | 65251 | II | 52 | F | 4.4 | 18.4 |
| 5 | * | * | * | * | * | * | * |
| 6 | BK | 7839 | II | 60 | F | 5.0 | 18.4 |
| 7 | BB | 762 | II | 60 | F | 4.4 | 17.1 |
| 8 | NM | 2634 | II | 59 | F | 4.4 | 18.4 |
| 9 | * | * | * | * | * | * | * |
| 10 | FS | 42040 | III | 25 | M | 4.4 | 18.4 |
| 11 | MS | 55073 | II | 32 | F | 5.0 | 18.4 |
| 12 | TH | 31639 | II | 65 | M | 4.0 | 17.1 |
| 13 | TP | 62225 | III | 46 | F | 5.0 | 18.4 |
| 14 | CS | 41984 | II | 52 | F | 4.4 | 18.4 |
| 15 | HF | 61346 | II | 33 | F | 4.4 | 16.0 |
| 16 | CK | 14351 | II | 51 | M | 4.4 | 17.1 |
| 17 | CM | 30094 | III | 46 | F | 5.0 | 17.1 |
| 18 | YK | 14546 | II | 55 | F | 4.4 | 81.4 |
| 19 | LB | 35242 | I | 37 | F | 4.0 | 18.4 |
| 20 | NB | 42473 | II | 51 | F | 4.4 | 18.4 |
| 21 | SC | 60754 | II | 53 | F | 4.4 | 16.0 |
| 22 | KS | 51704 | II | 55 | M | 5.0 | 18.4 |

TABLE 3-continued

Individual SPF Values

| Subject Number | Subject Initials | Subject ID # | Skin Type | Age | Sex | 8% HMS Standard | Hand and Body Wash with Sunscreen |
|---|---|---|---|---|---|---|---|
| 23 | BO | 41643 | II | 43 | F | 5.0 | 18.4 |
| 24 | EI | 61168 | III | 52 | F | 4.4 | 18.4 |
| Average SFF (n-20) | | | | | | 4.54 | 17.84 |
| Standard Deviation | | | | | | 0.33 | 0.85 |

Equipment to prepare the formulations noted herein may be taken from commonly available laboratory and commercial suppliers. Commonly used equipment includes blenders, mixers, grinders, and heaters along with variously sized storage and mixing containers. Other processing equipment for loading the finished product into desired retail containers may also be used.

The materials to manufacture the formulations noted herein are also taken from publicly available commercial suppliers. In certain instances, materials are commonly referred to by various trade names, and this has been noted, e.g., "Versene", "Germaben II", "Carbopol", "Sulfochem B-DEV", and "Span" products. These materials may be acquired from various suppliers known to people skilled in the art. Other materials are commonly referred to by their chemical names, e.g., soy, titanium dioxide, and water, and the like are so noted.

A key advantage of the body wash with sunscreen described herein relates to the manner of usage that the composition allows. The body wash composition may be applied by the human user during normal hygiene activities such as washing and/or showering. An effective amount of solar protective material remains on the user's skin even after the rinsing and washing has been completed. Thus, the user has applied to himself or herself, an amount of solar protective material during normal washing activities such as the morning shower. An additional or separate step of applying a greasy, sunblocking material is not required. The user can thus proceed through his daily activities such as recreation with the sunscreen material now applied to the body. Furthermore, and importantly, the testing described above indicates that an effective level of sunblocking material remains on the user's skin even after multiple rinsings. Thus, the user can confidently pursue activities such as water sports or exercises or any activity which might cause the user to perspire, and an effective level of sunscreen material will remain. Thus, it is believed that the compositions and formulations described herein provide an improved and convenient method for an active person to apply sunscreen material.

De-ionized water has been identified throughout this disclosure as a preferred water for the methods and formulations described herein. However, other kinds of water may be used, including water that has not been treated so as to be de-ionized. Tap water, spring water, municipal water, distilled water, bottled water, and the like may also be used in the methods and formulations described herein.

While the invention has been described with reference to a preferred embodiment or embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to a particular embodiment disclosed as the best mode contemplated for carrying out this invention, but that the invention will include all embodiments falling within the scope of the appended claims.

What is claimed is:

1. A method for creating a body wash with sunscreen, the method comprising the steps of:

blending water, with a first component of tetrasodium ethylenediaminetetracetate tetrahydrate, a second component of at least one of propylene glycol, diazolidinyl urea, and methylparaben and propylparaben, a third component of PEG 400, a fourth component of carbomer, and a fifth component of at least one of sodiuim laureth sulfate, cocamide DEA, and cocamidopropyl betaine, so as to create a first water phase;

blending at approximately 130 degrees F. dodecanoic acid, soy oil, 3,3,5-trimethylcyclohexyl 2-hydroxybenzoate, octyl methoxycinnamate, benzophenone-3, octylsalicylate, PEG-30 dipolyhydroxystearate, and titanium dioxide, so as to create a first oil phase;

combining the first oil phase with the first water phase so as to create an emulsion;

blending water with glyceryl stearate and PEG 100 stearate so as to create a second water phase; and blending the second water phase into the emulsion so as to create a body wash with sunscreen product, wherein the components are present in the body wash with sunscreen product in the following approximate amounts by weight percent:

| Chemical Name | % By Wt. |
| --- | --- |
| De-ionized water | balance |
| Tetrasodium ethhylenediaminetetraacetate tetrahydrate | 0.10-0.50 |
| Propylene Glycol (and) Diazolidinyl Urea (and) Methylparaben (and) Propylparaben | 0.25-1.50 |
| PEG 400 | 1.00-10.00 |
| Carbomer | 0.20-1.00 |
| Sodium Laureth Sulfate (and) Cocamide DEA (and) Cocamidopropyl Betaine | 10.00-60.00 |
| Dodecanoic Acid | 0.50-5.00 |
| Soy oil | 0.50-5.00 |
| 3,3,5-Trimethylcyclohexyl 2-hydroxybenzoate | 2.00-6.00 |
| Octyl methoxycinnamate | 2.00-6.00 |
| Benzophenone-3 | 2.00-6.00 |
| Octyl salicylate | 2.00-6.00 |
| PEG-30 dipolyhydroxystearate | 0.10-2.00 |
| Titanium dioxide | 0.0-4.00 |
| Glyceryl stearate (and) PEG 100 | 0.10-3.00. |

2. The method according to claim 1 wherein the step of blending water with a first component, a second component, a third component, a fourth component, and a fifth component so as to create a first water phase further comprises heating to at least approximately 130 degrees F.

3. The method according to claim 1 wherein the step of blending water with a first component, a second component, a third component, a fourth component, and a fifth component comprises heating water to at least approximately 130 degrees F., adding the first, second, and third component to the water and mixing; adding the fourth component and homogenizing so as to substantially eliminate lumps, and adding the fifth component and mixing.

4. The method according to claim 1 wherein the step of blending so as to create a first oil phase further comprises combining the dodecanoic acid, the soy oil, the 3,3,5-trimethylcyclohexyl 2-hydroxybenzoate, the octyl methoxycinnamate, the benzophenone-3, and the octyl salicylate components while heating to least approximately 130 degrees F. so as to homogenize the blend, adding PEG-30 dipolyhydroxystearate to the blend and mixing, and then adding titanium dioxide to the blend and mixing.

5. The method according to claim 1 wherein the step of combining the first water phase with the first oil phase is performed such that the first water phase and the first oil phase are at a temperature of from approximately 100 degrees F. to approximately 170 degrees F. when combined.

6. The method according to claim 5 further comprising milling the emulsion of the combined first water phase and first oil phase.

7. The method according to claim 6 wherein the milling progresses from approximately 10 to approximately 15 minutes.

8. The method according to claim 1 wherein the step of blending the second water phase further comprises adding the glyceryl stearate and PEG 100 stearate to water heated to approximately 185 degrees F. and mixing until dissolved.

9. The method according to claim 1 wherein the step of blending the second water phase with the emulsion so as to create a body wash with sunscreen product further comprises adding the emulsion to the second water phase and mixing until dissolved and further mixing until the temperature drops to approximately 110 degrees F.

10. The method according to claim 1 further comprising the step of blending fragrance into the body wash with sunscreen product at a weight percentage of between approximately 0.40 and 2.50.

11. A method for creating a body wash with sunscreen, the method comprising the steps of:

blending water, with a first component of tetrasodium ethylenediaminetetracetate tetrahydrate, a second component of at least one of propylene glycol, diazolidinyl urea, and methylparaben and propylparaben, a third component of PEG 400, a fourth component of carbomer, and a fifth component of at least one of sodiuim laureth sulfate, cocamide DEA, and cocamidopropyl retaine, so as to create a first water phase;

blending at approximately 130 degrees F. dodecanoic acid, soy oil, 3,3,5-trimethylcyclohexyl 2-hydroxybenzoate, octyl methoxycinnamate, benzophenone-3, octylsalicylate, sorbitan monolaurate, sorbitan trioleate, and titanium dioxide, so as to create a first oil phase;

combining the first oil phase with the first water phase so as to create an emulsion;

blending water with glyceryl stearate and PEG 100 stearate so as to create a second water phase; and blending the second water phase with the emulsion so as to create a body wash with sunscreen product, wherein the components are present in the body wash with sunscreen product in the following approximate amounts by weight percent:

| Chemical Name | % By Wt. |
| --- | --- |
| De-ionized water | balance |
| Tetrasodium ethhylenediaminetetraacetate tetrahydrate | 0.10-0.50 |
| Propylene Glycol (and) Diazolidinyl Urea (and) Methylparaben (and) Propylparaben | 0.25-1.50 |
| PEG 400 | 1.00-10.00 |
| Carbomer | 0.20-1.00 |
| Sodium Laureth Sulfate (and) Cocamide | 10.00-60.00 |

-continued

| Chemical Name | % By Wt. |
|---|---|
| DEA (and) Cocamidopropyl Betaine | |
| Dodecanoic Acid | 0.50-5.00 |
| Soy oil | 0.50-5.00 |
| 3,3,5-Trimethylcyclohexyl 2-hydroxybenzoate | 2.00-6.00 |
| Octyl methoxycinnamate | 2.00-6.00 |
| Benzophenone-3 | 2.00-6.00 |
| Octyl salicylate | 2.00-6.00 |
| Sorbitan monolaurate | 0.01-1.00 |
| Sorbitan trioleate | 0.01-1.00 |
| Titanium dioxide | 0.00-4.00 |
| Glyceryl stearate (and) PEG 100 stearate | 0.10-3.00. |

12. The method according to claim 11 wherein sorbitan monopalmitate and sorbitan monostearate are substituted for sorbitan monolaurate and sorbitan trioleate.

13. The method according to claim 11 wherein the step of blending water with a first component, a second component, a third component, a fourth component, and a fifth component so as to create a first water phase further comprises heating to at least approximately 130 degrees F.

14. The method according to claim 11 wherein the step of blending so as to create a first oil phase further comprises combining the dodecanoic acid, the soy oil, the 3,3,5-trimethylcyclohelxyl 2-hydroxybenzoate, the octyl methoxycinnamate, the benzophenone-3, and the octyl salicylate components while heating to approximately 130 degrees F. so as to homogenize the blend, adding sorbitan monolaurate and sorbitan trioleate to the blend and mixing, and then adding titanium dioxide to the blend and mixing.

15. The method according to claim 11 wherein the step of combining the first water phase with the first oil phase is performed such that the first water phase and the first oil phase are at a temperature of from approximately 100 degrees F. to approximately 170 degrees F. when combined.

16. The method according to claim 15 further comprising milling the emulsion of the combined first water phase and first oil phase.

17. The method according to claim 16 wherein the milling progresses from approximately 10 to approximately 15 minutes.

18. The method according to claim 11 further comprising the step of blending fragrance into the body wash with sunscreen product at a weight percentage of between approximately 0.40 and 2.50.

19. A method for creating a body wash with sunscreen, the method comprising the steps of:
blending water, with a first component of tetrasodium ethylenediaminetraacetate tetrahydrate, a second component of PEG 400, and a third component of at least one of sodium laureth sulfate, cocamide MEA, and cocamidopropyl betaine, followed by slowly dispersing titanium dioxide, so as to create a first water phase;
blending dodecanoic acid, soy oil, 3,3,5-trimethylcyclohexyl 2-hydroxybenzoate, octyl methoxycinnamate, benzophenone-3, and octyl salicylate so as to create a first oil phase;
combining the first oil phase and the first water phase and adding sorbitan monolaurate and sorbitan trioleate so as to create an emulsion;
adding benzyl alcohol and methylchloroisothiazolinone and methylisothiazolinone, and viscositiy modifier to said emulsion;
optionally adding fragrance to said emulsion;
blending water with glyceryl stearate and PEG 100 stearate so as to create a second water phase; and
blending the second water phase into the combined composition so as to create a body wash with sunscreen product, wherein the components are present in the product in the following approximate amounts by weight percent:

| Order | Chemical Name | % By Wt. |
|---|---|---|
| 1 | Water | balance |
| 2 | Tetrasodium ethhylenediaminetetraacetate tetrahydrate | 0.10-0.50 |
| 3 | Polyethylene glycol 400 | 1.00-10.00 |
| 4 | Sodium Laureth Sulfate (and) Cocamide MEA (and) Cocamidopropyl Betaine | 10.00-50.00 |
| 5 | Titanium dioxide (and) hydrated silica (and) aluminum hydroxide (and) dimethicone/methicone copolymer | 0.0-4.00 |
| 6 | Dodecanoic Acid | 0.50-5.00 |
| 7 | Soy oil | 0.50-5.00 |
| 8 | 3,3,5-Trimethylcyclohexyl 2-hydroxybenzoate | 2.00-6.00 |
| 9 | Octyl methoxycinnamate | 2.00-6.00 |
| 10 | Benzophenone-3 | 2.00-6.00 |
| 11 | Octyl salicylate | 2.00-6.00 |
| 12 | Sorbitan monolaurate | 0.01-1.50 |
| 13 | Sorbitan trioleate | 0.01-1.50 |
| 14 | Benzyl alcohol (and) methylchloroisothiazolinone (and) methylisothiazolinone | 0.05-1.75 |
| 15 | Fragrance | 0.0-2.50 |
| 16 | Viscosity modifier | 0.01-1.00 |
| 17 | Glyceryl stearate (and) PEG 100 | 0.10-3.00. |

* * * * *